United States Patent [19]

Hoelscher et al.

[11] Patent Number: 5,288,877

[45] Date of Patent: Feb. 22, 1994

[54] CONTINUOUS PROCESS FOR PREPARING INDOLENINE COMPOUNDS

[75] Inventors: Charles H. Hoelscher, Murrysville; Bruce R. Anderson, Irwin, both of Pa.

[73] Assignee: PPG Industries, Inc., Pittsburgh, Pa.

[21] Appl. No.: 725,849

[22] Filed: Jul. 3, 1991

[51] Int. Cl.$^5$ ............................................ C07D 209/08
[52] U.S. Cl. .................................... 548/490; 548/411; 548/491
[58] Field of Search ...................... 548/490, 411, 491

[56] References Cited

U.S. PATENT DOCUMENTS

| | | | |
|---|---|---|---|
| 3,562,172 | 2/1971 | Ono et al. | 252/300 |
| 3,639,420 | 2/1972 | Illy et al. | 260/319.1 |
| 4,062,865 | 12/1977 | Moggi | 260/319.1 |
| 4,240,963 | 12/1980 | Laas et al. | 260/319.1 |
| 4,637,698 | 1/1987 | Kwak et al. | 351/163 |
| 4,816,584 | 3/1989 | Kwak et al. | 544/71 |
| 4,830,786 | 5/1989 | Pease et al. | 260/396 |
| 4,931,219 | 6/1990 | Kwiatkowski et al. | 252/385 |

OTHER PUBLICATIONS

Houlihan, *Indoles, Part One* pp. 257–258, 1972.
"Direct Synthesis of Indole by the Fischer Indole Synthesis", by Masao Nakazaki et al, J. Org. Chem., vol. 41, No. 10, 1976.
"Fischer Indole Synthesis on Unsymmetrical Ketones. The Effect of the Acid Catalyst", by M. H. Palmer et al, J. Chem. Soc. (B), pp. 446–449 (1969).
"One-Step Synthesis of 1,2,3,4-Tetrahydrocarbazole and 1,2-Benzo-3,4-dihydrocarbazole", by C. Rogers et al, JACS, vol. 69, p. 2910 (1947).
"Direction of Cyclization in the Fischer Indole Synthesis. Mechanistic Consideration", by F. M. Miller et al, J. Org. Chem., vol. 43, No. 17, pp. 3384–3387 (1978).

*Primary Examiner*—Robert W. Ramsuer
*Assistant Examiner*—Jacqueline Haley
*Attorney, Agent, or Firm*—Irwin M. Stein

[57] ABSTRACT

Described is a continuous process for preparing indolenine compounds which comprises charging continuously and simultaneously to a reactor containing an acetic acid reaction medium (1) substituted phenylhydrazine and (2) unsymmetrical ketone from separate sources, continuously discharging from the reactor indolenine product in acetic acid solution, separating acetic acid from the indolenine product, recycling separated acetic acid to the reactor, neutralizing residual acetic acid remaining in the indolenine product with aqueous inorganic alkaline reagent, and separating from the indolenine product an aqueous solution of salts resulting from the preparation and neutralization of the indolenine product.

21 Claims, No Drawings

CONTINUOUS PROCESS FOR PREPARING INDOLENINE COMPOUNDS

DESCRIPTION OF THE INVENTION

Spiro(indolino)-type compounds have been described as possessing photochromic properties and have been suggested for use in applications in which a color change or darkening induced by sunlight is a desirable feature. For example, spiro(indolino) naphthoxazine compounds are described in U.S. Pat. Nos. 3,562,172, 3,578,602, 4,215,010 and 4,342,668. Spiro(indolino) pyridobenzoxazines have been described in U.S. Pat. No. 4,637,698. Spiro(indolino) benzoxazines have been described in U.S. Pat. No. 4,816,584. Spiro(benzindolino)-type compounds have been described in U.S. Pat. No. 4,931,219.

The aforedescribed spiro(indolino)-type compounds are commonly prepared by reacting the corresponding Fischer's base (indolenine) reactant with an aromatic reactant, e.g., 5-nitroso (or formal)-6-hydroxy quinoline or 1-nitroso (or formal)-2-hydroxy naphthalene. The Fishcher's base reactant may be prepared by intramolecular condensation of an appropriately substituted phenylhydrazine, e.g., a phenylhydrazine hydrochloride, with an appropriate unsymmetrical ketone in the presence of an acid catalyst, e.g., zinc chloride, acetic acid, alcoholic sulfuric acid or a combination of acids. The aforedescribed intramolecular condensation reaction is highly exothermic and, therefore, great care must be observed in performing the reaction.

The Fischer indole synthesis, i.e., the condensation of a phenylhydrazine with an unsymmetrical ketone, is typically described as a batch process involving relatively small amounts of reactant materials. In such circumstances, the rapid and large reaction exotherm, which is estimated to be on the order of 36–40 KCal/mole, can be handled safely. However, when larger quantities of indolenine compounds are required, use of relatively small multiple batch preparations is inefficient and not cost effective. Larger batch preparations of indolenines are not attractive because of the difficulty of handling the large reaction exotherm which accompanies large batch preparations and the potential for runaway reactions in such circumstances. There has developed, therefore, a need for a safe procedure for large scale preparation of indolenine compounds.

It has now been discovered that indolenine compounds may be synthesized safely and continuously by a method which comprises continuously charging phenylhydrazine and unsymmetrical ketone reactants simultaneously to a reactor containing a reaction medium including a weak organic carboxylic acid, e.g., acetic acid, and continuously removing the resultant indolenine product from the reactor dissolved in the reaction medium. The reaction medium and carboxylic acid is separated from the indolenine product and recycled to the reactor. The indolenine product is neutralized with alkaline reagent and salts resulting from the preparation and neutralization thereof are separated from the neutralized indolenine product. Indolenine compounds prepared in accordance with the foregoing continuous process may be used to prepared indoleninium halides which may be condensed with an aromatic reactant to produce spiro(indolino)-type compounds as described hereinabove.

DETAILED DESCRIPTION OF THE INVENTION

Indolenine materials that may be prepared in accordance with the process described herein may be represented by the following graphic formula:

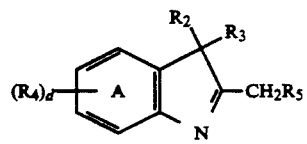

I

In graphic formula I, $R_2$ and $R_3$ may each be selected from the group consisting of $C_1$–$C_5$ alkyl, phenyl, mono- and di-substituted phenyl, benzyl or $R_2$ and $R_3$ may combine to form an alicyclic ring containing from 6 to 8 carbon atoms (including the spiro carbon atom), norbornyl and adamantyl. The aforesaid phenyl substituents may be selected from $C_1$–$C_4$ alkyl, e.g., methyl, ethyl, propyl and butyl, and $C_1$–$C_5$ alkoxy, e.g., methoxy, ethoxy, propoxy, butoxy and pentoxy radicals. More particularly, $R_2$ and $R_3$ may each be selected from $C_1$–$C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

In graphic formula I, each $R_4$ may be selected from $C_1$–$C_5$ alkyl, halogen, e.g., chloro and fluoro, $C_1$–$C_5$ alkoxy, nitro, cyano, $C_1$–$C_4$ monohaloalkyl, e.g., chloromethyl, fluoromethyl, chloroethyl, chloropropyl, etc., $C_1$–$C_4$ polyhaloalkyl, e.g., trihaloalkyl such as trifluoromethyl, $C_1$–$C_8$ alkoxycarbonyl, and $C_1$–$C_4$ acyloxy, i.e., $R_cC(O)O$—, wherein $R_c$ is a $C_1$–$C_4$ alkyl, e.g., methyl. The letter "d" in graphic formula I represents an integer that may vary from 0 to 4, e.g., 0 to 2, such as 1 or 2, and denotes the number of non-hydrogen substituents. Preferably, each $R_4$ is selected from the group consisting of $C_1$–$C_2$ alkyl, chloro, fluoro, $C_1$–$C_2$ trihaloalkyl, e.g., trihalomethyl such as trifluoromethyl, and $C_1$–$C_2$ alkoxy. When "d" is 0 (zero), there are no $R_4$ substituents and all of the aromatic carbon atoms have their full complement of hydrogen atoms for the indole group.

In a further embodiment, $(R_4)_d$ is an aromatic ring system, e.g., a benzene ring, fused to ring A, said ring system optionally carrying one or more, e.g., one or two, substituents, $(R_6)_e$, each of the $R_6$ substituents being the same as defined above for the non-fused ring substituents $R_4$. The letter "e" is preferably the integer 0, 1 or 2.

In graphic formula I, $R_5$ may be selected from the group consisting of hydrogen, methoxy, and $C_1$–$C_2$ alkyl, i.e., methyl or ethyl. Preferably, $R_5$ is hydrogen.

The phenylhydrazine reactant is preferably used as the hydrochloride salt since the phenylhydrazine reagents are unstable, and may be represented by the following graphic formula:

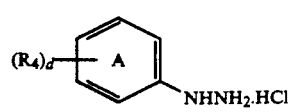

II

In graphic formula II, A, $R_4$ and d are the same as defined with respect to graphic formula I.

The unsymmetrical ketone reactant may be represented by the following graphic formula:

$$R_5CH_2—C(O)—CH(R_3)R_2 \qquad III$$

wherein $R_2$, $R_3$ and $R_5$ are the same as described herein with respect to graphic formula I.

The ratio of phenylhydrazine reactant to the unsymmetrical ketone reactant can, of course, vary. Since the intramolecular condensation reaction is an equimolar reaction, it is preferred that about stoichiometric molar amounts of the reactants be used. Preferably, the phenylhydrazine reactant is reacted completely. Typically, the mole ratio of unsymmetrical ketone to phenylhydrazine will range from about 1.2:1 to about 1:1. To insure complete utilization of the phenylhydrazine, the ketone reactant is preferably used in slight molar excess.

The condensation reaction is initiated at the minimum temperatures at which the intramolecular condensation reaction readily occurs. The herein described process design insures that there is a relatively small amount of unreacted reagents present in the reactor at any one time. Therefore, the large exotherm which would accompany a large batch reaction is eliminated. Additionally, control of the reaction exotherm can be attained readily by jacketing the reactor and passing a heat exchange fluid, e.g., a constant temperature bath through the jacket.

In the herein described process, the contents of the reactor are heated, e.g., by the heat exchange fluid, to a temperature at which the condensation reaction is initiated. Such initiation temperatures may vary from about 50° C. to about 80° C., e.g., 75° C. Thereafter, the reaction temperature is controlled by the circulating constant temperature heat exchange fluid passing through the jacket surrounding the reactor. Reaction temperatures of from about 75° C. to about 100° C. for the condensation reaction are typically observed. Reaction temperatures below 75° C. may be used; however, such temperatures result in prolonged retention times, which requires larger reaction vessels. Typically, retention times will average about 30 minutes at reaction temperatures of 75° C. to 100° C.

The reaction medium in which the condensation reaction is conducted is an organic solvent including a weak organic carboxylic acid. It is contemplated and preferred that the organic solvent is the organic carboxylic acid, e.g., acetic acid; however, the acid may be a constituent of the reaction medium. Use of the carboxylic acid as the organic solvent provides the further benefit of a homogeneous reaction medium.

When the reaction medium comprises an organic solvent (other than the carboxylic acid), it is preferred that such solvent be inert (non-reactive) with the reagents and the resulting product; have a boiling point above 50° C.; serve to solubilize the indolenine product; and more preferably, form an azeotrope with the carboxylic acid.

Examples of non-carboxylic acid materials that may comprise the reaction medium include paraffinic hydrocarbons containing from 6 to 10 carbon atoms, e.g., the heptanes, aromatic hydrocarbons such as benzene, alkyl substituted benzenes, such as toluene, xylene and mesitylene, dialkyl ethers containing greater than 4 carbon atoms in the alkyl group, such as dibutyl ether, cyclic hydrocarbon ethers, and tetrahydrofuran.

The organic carboxylic acid, e.g., monocarboxylic acid, used in or as the reaction medium is a weak acid. Strong organic and mineral acids tend to cause the formation of indole by-product rather than the desired indolenine product, thereby reducing the yield of the desired indolenine product. One skilled in the art can readily ascertain by reference to handbooks and accepted classification standards suitable weak carboxylic acids.

Examples of carboxylic acids that may be used in the described method include formic, acetic, propionic and butyric acids. Preferably, the acid used is acetic acid. The acid serves as the catalyst for the reaction and when used alone, also serves as the solvent, i.e., the reaction medium. In the latter embodiment, separation and recycling of the solvent, e.g., acetic acid, from the indolenine product is simplified.

When used with another organic solvent, e.g., n-heptane, sufficient of the carboxylic acid is used to serve as the catalyst for the condensation reaction, i.e., catalytic amounts. Generally, from 0.1 to 3, e.g., 1.1 to 3, moles of the carboxylic acid per mole of phenylhydrazine hydrochloride reactant is used. When the carboxylic acid is used as the reaction medium, a large catalytic excess of the acid is, of course, used. An example of a mixed solvent is n-heptane containing about 10 weight percent acetic acid. This mixture of materials forms an azeotrope which may be readily separated from the indolenine product and recycled to the reactor. Use of a mixed solvent system as the reaction medium may however complicate the means required to separate it from the indolenine product and recycle the solvent system to the reactor.

In accordance with the process described herein, a separate reactant feed source with feed control means for each of the reagents is located near the reactor vessel. One reactant feed source container contains the unsymmetrical ketone, which is usually a liquid and, therefore, can be readily pumped to the reactor. The other reactant feed source container is charged with the phenylhydrazine reagent. The phenylhydrazine reagent is preferably charged as a slurry in the reaction medium, which preferably is acetic acid; but may be charged as a dry solid, although such an embodiment is less preferred as providing less control of the amounts charged to the reactor. Use of such a slurry facilitates pumping of the phenylhydrazine reagent in a controlled manner to the reactor and can also provide the means for charging make-up reaction medium to the reactor. Control means, such as adjustable feed pumps, are attached to the feed lines of each reactant to control and monitor the amount of reactant charged to the reactor to provide the desired molar amount of each that is charged into the reactor.

Feed lines from the respective reactant feed sources, e.g., a feed tank, to the reactor may be independent. In a modification of such embodiment, the feed lines can join at a point near the reactor to form a common feed line that introduces a mixture of the phenylhydrazine and unsymmetrical ketone reagents into the reactor. In the latter case, the amount of both reactants present in the mixture in the common feed line is small. Moreover, the mixture is usually at ambient temperatures, i.e., temperatures below reaction temperature, and is present as a mixture external to the reactor for a very short period of time, thereby eliminating any potential hazard from premixing of the reactants. Typically, the reactants are introduced below the liquid level of the reaction medium, e.g., by a dip feed tube.

It is contemplated that if separate feed vessels for the phenylhydrazine and ketone reactants are unavailable, a mixture (in an appropriate molar ratio) of the reactants in a single storage vessel may be used. This embodiment is, however, not preferred since the mixture would pose potentially a hazardous condition. The single storage vessel should, in the aforesaid case, have cooling means associated with it to maintain the mixture well below reaction temperatures.

The reactor is preferably equipped with a conventional reflux condenser for returning vaporized reactant materials to the reactor; a mechanical stirrer; and means for introducing an inert gas, e.g., nitrogen, for providing an inert gas pad or purge. To commence the process described herein, the reactor is typically charged with an initial charge of the reaction medium, e.g., acetic acid, that is sufficient to cover the bottom of the inlet feed tube; the reaction medium in the reactor is heated to a temperature at which the reaction will self initiate, e.g., by the heat exchange fluid in the jacket of the reactor; and the reactants then charged at predetermined rates to the heated and agitated reaction medium. When the reactor has reached a desired operating volume, indolenine product in the reaction medium, e.g., acetic acid, is continuously and controllably removed from the reactor so as to maintain a constant volume in the reactor.

In an alternative embodiment of the process, the liquid reaction product removed from the reactor may be first filtered to separate solid by-product salt, e.g., ammonium chloride, from the reaction medium. However, this is less preferred since such salt is soluble in water and may be removed as an aqueous solution in a subsequent step. Moreover, the presence of the salt in the aqueous phase increases the density of the aqueous phase and reduces the solubility of the indolenine product in the aqueous phase, thereby improving the yield of the indolenine product.

The liquid reaction product from the reactor (preferably also containing ammonium chloride by-product salt) is forwarded to a receiving vessel equipped with heating means, nitrogen purge and a condenser. The reaction medium, e.g., acetic acid, is separated, e.g., distilled from the receiving vessel, condensed and recycled eventually to the reactor. Recycled reaction medium may be forwarded to the phenylhydrazine feed tank, directly to the reactor, or to both the phenylhydrazine feed tank and the reactor. The amount of reaction medium recycled is controlled to maintain the volume of liquid in the reactor at the desired level. When the carboxylic acid is not the reaction medium or is not separated from the indolenine product as an azeotrope with the organic (non-acid) solvent, it may be necessary to make-up the appropriate reaction medium from recovered elements of the reaction medium before recycling it to the reactor and/or using it to make-up further phenylhydrazine slurry reagent.

The receiving vessel into which the liquid reaction product discharged from the reactor is introduced may be operated continuously or as a batch process step.

The indolenine product from which the reaction medium has been removed, e.g., distilled, is neutralized, e.g., to a pH of about 7, with an aqueous inorganic alkaline reagent, e.g., sodium hydroxide, and the resultant carboxylic acid salt produced by the neutralization step, e.g., the acetate salt, (and preferably the ammonium chloride by-product salt) separated from the indolenine product, e.g., by dissolution in the aqueous phase of the alkaline reagent, which aqueous phase is decanted from the organic phase, i.e., the indolenine product. Additional conventional workup procedures of the indolenine product provide a purified material that may be used to produce indoleninium halides.

Inorganic alkaline reagents that may be used should be water-soluble at the temperatures at which neutralization is conducted and form salts that are sufficiently water soluble to be dissolved in the aqueous phase formed by use of the aqueous alkaline reagent. Example of suitable inorganic alkaline reagents include the hydroxides, carbonates and bicarbonates of Group 1a metals, e.g., lithium, sodium and potassium and the hydroxides of calcium, magnesium and barium. Group 1a metal alkaline reagents, e.g., sodium hydroxide, are preferred because of their cost, availability, and the water solubility of the salts produced by neutralization, e.g., sodium acetate.

The present invention is more particularly described in the following examples which are intended as illustrative only since numerous modifications and variations therein will be apparent to those skilled in the art.

EXAMPLE

A two-liter, 3-necked jacketed glass reactor was charged with 350 milliliters (ml) of acetic acid. The reactor was fitted with a feed tube, thermometer, reflux condenser, nitrogen purge and mechanical stirrer. The reactor jacket was supplied heat or cooling by a constant temperature heat exchange fluid comprising a 50/50 ethylene glycol/water mixture circulating through the jacket around the reactor. The reactor was fitted with a bottom discharge which was connected to a pump that provided control of the amount of liquid reactor discharge removed from the reactor. Located adjacent to the reactor were two reactant feed containers, the first of which was charged with a slurry of dimethyl phenylhydrazine hydrochloride (10.0 gram moles) and glacial acetic acid (7 liters). The second reactant feed container was charged with 3-methyl-2-pentanone (10.08 gram moles). Connected to each reactant feed container was a feed line for transferring reactant to the reactor. Each feed line contained a feed pump. The feed lines from the reactant feed containers joined near the reactor to form a common reactant feed line terminating in a feed dip tube, the end of which was below the level of the acetic acid in the reactor.

The initial charge of acetic acid in the reactor was heated to 75° C. Reactant materials from the feed containers were then forwarded by the reactant feed pumps to the reactor at respective rates of 45 grams/minute of hydrazine hydrochloride slurry and 6.63 grams/minute of 3-methyl-2-pentanone. The mole ratio of the ketone to phenylhydrazine charged to the reactor was 1.17:1. After the reactor had reached an operating volume of 1.5 liters, the reactor discharge pump was started and set to maintain a constant volume of 1.5 liters in the reactor. The average retention time of the reactants in the reactor was calculated to be about 30 minutes.

Reactor product was discharged into a receiving vessel, which was set in a heating mantle and fitted with a stirrer, nitrogen purge and condenser. Reactor discharge in the receiving vessel was maintained under nitrogen at 60° C. with constant stirring. Subsequently, the receiving vessel was fitted with a distillation column, distillate receiver and a controlled vacuum source.

A vacuum was applied to the receiving vessel system and acetic acid distilled from the product mixture at approximately a 65° C. head temperature and a pressure of 27 inches of mercury. Distillation continued until the pot temperature reached 100° C., at which time the distillation was stopped and the receiving vessel cooled and vented with nitrogen. A total of 6,360 grams of acetic acid distillate was recovered.

The receiving vessel containing the acetic acid depleted indolenine product was chilled in an ice bath and then diluted with two liters of deionized water and one liter of n-heptane. Acetic acid remaining in the product was neutralized by dropwise addition of 1078 grams of a 50 percent sodium hydroxide solution. The resultant material in the holding vessel contained solid salt which was dissolved by the addition of two liters of water. The organic phase was separated and washed with 500 milliliters of water three times to a pH of 7.0. The aqueous phase and water washes were back extracted with one liter of n-heptane two times. The combined organics were dried over magnesium sulfate and filtered through a fritted glass Buchner funnel. N-heptane was stripped from the product at 75° C. and a vacuum of 27 inches of mercury. The product, a mixture of 2,3,4,5 (and 2,3,5,6)-tetramethyl-3-ethyl-indolenine was obtained in 97.5 percent yield (basis the hydrazine charged). The product assayed 96.7 percent by GC (gas chromatograph) analysis. A mixture of products is obtained because of the alternate way in which the intramolecular condensation reaction can occur.

COMPARATIVE EXAMPLE 1

A three-necked flask equipped with stirrer, nitrogen purge, thermometer and fitted with a modified Clasien head and condenser was charged with glacial acetic acid (2500.0 grams), 3,4-dimethyl phenylhydrazine hydrochloride (865.0 grams, 5.00 gram moles) and 3-methyl-2-pentanone (525.4 grams, 5.25 gram moles). With continuous stirring and nitrogen purge, the reaction mixture was carefully heated at a rate of 0.5° C. per minute. When the temperature of the reaction mixture reached 50°-55° C., heating was discontinued. The reaction mixture changed in color from a silver-gray slurry to a dark red solution containing off-white crystals. This change in color was attended by a rapid temperature increase from approximately 0.5° C. per minute to more than 10° C. per minute. The temperature of the reaction mixture was allowed to increase to the boiling point of acetic acid (120° C.) and reflux from the condenser diverted into a condensate receiver. After the reaction exotherm had subsided, the reaction mixture was stirred for a period of 30 minutes. A short distillation column was added between the flask and reflux condenser, a vacuum applied and acetic acid distilled from the reaction mixture in the condensate receiver. A total of 2326 grams of acetic acid was recovered.

The reaction flask was cooled in an ice bath, diluted with 2 liters of water and the remaining acetic acid in the reaction mixture neutralized at 25° C. by dropwise addition of a 50 percent sodium hydroxide solution (635 grams, 7.93 gram moles). The reaction mixture was transferred under nitrogen to a separatory funnel, left standing overnight and subsequently phase separated. The aqueous phase was extracted twice with 500 milliliters of n-heptane and then once with 250 milliliters of n-heptane. All of the organic phases were combined and washed with 500 milliliters of water three times. The final wash water had a measured pH of 7.0.

The combined aqueous wash solutions were back extracted with 500 milliliters of n-heptane. The combined organic phases were dried for approximately 30 minutes over 250 grams of anhydrous magnesium sulfate. The magnesium sulfate was separated from the organic phase by filtration. The n-heptane solvent was stripped from the product, a mixture of 2,3,4,5(and 2,3,5,6)-tetramethyl-3-ethyl-indolenine, which was obtained in 91.2 percent yield (basis the hydrazine charged). The product assayed about 91.59 percent by GC analysis.

COMPARATIVE EXAMPLE 2

A jacketed three-necked reaction flask was fitted with a mechanical stirrer, a thermometer, nitrogen purge, condenser feed tube and a bottom discharge stopcock. The reactor jacket was connected to a constant temperature circulating bath. A liquid addition burette was fitted to one of the reactor flask's necks. Acetic acid (578 grams) and 3,4-dimethyl phenylhydrazine hydrochloride (172.7 grams) were charged to the reaction flask. 3-methyl-2-pentanone (106.2 grams) was charged to the addition burette.

The reaction flask containing the acetic acid and 3,4-dimethyl phenylhydrazine hydrochloride was heated to 79° C. at which time 3-methyl-2-pentanone was added dropwise from the addition burette over the next 30 minutes. After approximately 10 minutes, the temperature in the reaction flask had increased to 85° C. and the slurry turned dark red. During the next 3–5 minutes, the reaction temperature had increased to 105° C. After all of the 3-methyl-2-pentanone had been added, the reaction mixture was held at 80° C. for a total of 70 minutes. The reaction flask contents were cooled to about 25° C., transferred to a separatory funnel and diluted with 2 liters of water and 1 liter of n-heptane. The resultant mixture was mixed thoroughly and allowed to stand for approximately 15 minutes. The mixture was phase separated and the organic phase washed sequentially with 250 milliliters of water, 350 milliliters of a 3 percent sodium hydroxide solution, 250 milliliters of water and then 500 milliliters of water. The aqueous phases were combined and back-extracted with 500 milliliters of n-heptane. The organic phases were combined and n-heptane removed at 70° C. and a pressure of 26 inches of mercury. The recovered product, a mixture of 2,3,4,5(and 2,3,5,6)-tetramethyl-3-ethyl-indolenine was obtained in 77.6 percent yield (basis the hydrazine charged). The product assayed 90.49 percent by GC analysis.

Although the present invention has been described with reference to the specific details of particular embodiments, it not intended that such details be regarded as limitations upon the scope of the invention except as and to the extent that they are included in the accompanying claims.

We claim:

1. In the method for preparing an indolenine compound by intramolecular condensation of a phenylhydrazine with an unsymmetrical ketone, the improvement which comprises the steps of:
   (a) continuously and simultaneously introducing (1) phenylhydrazine reactant and (2) unsymmetrical ketone reactant from separate sources into a reactor having a reaction medium consisting essentially of organic solvent, (b) carrying out said intramolecular condensation in said reaction medium in the presence of a catalyst consisting essentially of a catalytic amount of a weak organic carboxylic acid and at temperatures at which the condensation reaction occurs, (c) continuously removing indolenine product from the reactor as a solution in said reaction medium, and (d) separating indolenine product from the reaction medium solution thereof removed from the reactor.

2. The method of claim 1 comprising the further steps of:

(a) neutralizing residual organic carboxylic acid remaining in the indolenine product with aqueous inorganic alkaline reagent, and (b) separating from the indolenine product an aqueous solution of salts resulting from the preparation and neutralization of said product.

3. The method of claim 1 comprising the further step of returning to the reactor reaction medium separated from the indolenine product in step (d).

4. The method of claim 1 comprising the added step of separating solid by-product salt from the solution of indolenine product removed from the reactor in step (c).

5. The method of claim 1 wherein the phenylhydrazine reactant is represented by the graphic formula,

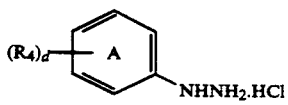

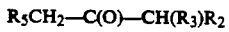

wherein each $R_4$ is selected from the group consisting of (i) $C_1$–$C_5$ alkyl, halogen, $C_1$–$C_5$ alkoxy, nitro, cyano, $C_1$–$C_4$ monohaloalkyl, $C_1$–$C_4$ polyhaloalkyl, $C_1$–$C_8$ alkoxycarbonyl, and $C_1$–$C_4$ acyloxy, and (ii) $(R_4)_d$ is an aromatic ring fused to ring A, said aromatic ring optionally having one or more substituents, $(R_6)_e$, each of said $R_6$ substituents being the same as defined for $R_4$, "d" is an integer of from 0 to 4, and "e" is an integer of from 0 to 2.

6. The method of claim 1 wherein the unsymmetrical ketone reactant is represented by the graphic formula, $$R_5CH_2-C(O)-CH(R_3)R_2$$

wherein:

(a) $R_2$ and $R_3$ are each selected from the group consisting of $C_1$–$C_5$ alkyl, phenyl, mono- and di-substituted phenyl, benzyl, or $R_2$ and $R_3$ combine to form a group selected from the group consisting of an alicyclic ring containing from 6 to 8 carbon atoms (including the spiro carbon atoms), norbornyl and adamantyl, said phenyl substituents being selected from the group consisting of $C_1$–$C_4$ alkyl and $C_1$–$C_5$ alkoxy, and (b) $R_5$ is selected from the group consisting of hydrogen, methoxy and $C_1$–$C_2$ alkyl.

7. The method of claim 5 wherein each $R_4$ is selected from the group consisting of $C_1$–$C_2$ alkyl, chloro, fluoro, $C_1$–$C_2$ alkoxy and $C_1$–$C_2$ trihaloalkyl, and d is an integer of from 0 to 2.

8. The method of claim 6 wherein $R_2$ and $R_3$ are each selected from the group consisting of $C_1$–$C_5$ alkyl and phenyl, and $R_5$ is hydrogen.

9. The method of claim 1 wherein the mole ratio of the ketone reactant to the phenylhydrazine reactant varies from about 1.2:1 to about 1:1.

10. The method of claim 1 wherein the reaction medium consists essentially of the weak organic carboxylic acid.

11. The method of claim 10 wherein the carboxylic acid is acetic acid.

12. The method of claim 2 wherein the inorganic alkaline reagent is selected from the group consisting of the hydroxides, carbonates and bicarbonates of the metals lithium, sodium or potassium.

13. In the method for preparing an indolenine compound by intramolecular condensation of a phenylhydrazine with an unsymmetrical ketone, the improvement which comprises the steps of:

(a) continuously and simultaneously introducing (1) phenylhydrazine reactant and (2) unsymmetrical ketone reactant from separate sources to a reactor having a reaction medium consisting essentially of organic solvent, at temperatures at which the condensation reaction occurs, (b) carrying out said intramolecular condensation in said reaction medium in the presence of a catalyst consisting essentially of a catalytic amount of weak organic carboxylic acid, (c) continuously removing indolenine product from the reactor as a solution in said reaction medium, (d) separating indolenine product from the reaction medium solution removed from the reactor, (e) returning to the reactor reaction medium separated from the indolenine product in step (c), (f) neutralizing residual organic carboxylic acid remaining in the indolenine product with aqueous inorganic alkaline reagent, and (g) separating from the indolenine product of step (f) an aqueous solution of salts resulting from the preparation and neutralization of said product.

14. The method of claim 13 wherein the reaction medium consists essentially of weak organic carboxylic acid.

15. The method of claim 13 wherein the reaction medium is a heptane-weak organic carboxylic acid mixture.

16. The method of claim 14 wherein the phenylhydrazine reactant is represented by the graphic formula,

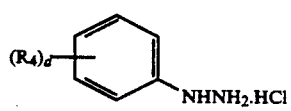

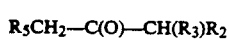

wherein $R_4$ is selected from the group consisting of $C_1$–$C_2$ alkyl, chloro, fluoro, $C_1$–$C_2$ alkoxy and $C_1$–$C_2$ trihaloalkyl, and d is an integer of from 0 to 2, and the unsymmetrical ketone reactant is represented by the graphic formula, $$R_5CH_2-C(O)-CH(R_3)R_2$$

wherein $R_2$ and $R_3$ are each selected from the group consisting of $C_1$–$C_5$ alkyl and phenyl, and $R_5$ is hydrogen.

17. The method of claim 16 wherein the carboxylic acid is acetic acid.

18. The method of claim 17 wherein the mole ratio of ketone reactant to phenylhydrazine reactant is from about 1.2:1 to about 1:1.

19. The method of claim 17 wherein the inorganic alkaline reagent is selected from the group consisting of the hydroxides, carbonates and bicarbonates of sodium or potassium.

20. The method of claim 17 wherein the intramolecular condensation reaction temperature is from about 75° C. to about 100° C.

21. The method of claim 1 wherein the intramolecular condensation reaction temperature is from about 75° C. to about 100° C.

* * * * *